(12) United States Patent
Kuhn

(10) Patent No.: US 7,140,880 B2
(45) Date of Patent: Nov. 28, 2006

(54) MEDICAL OR DENTAL-MEDICAL HANDPIECE HAVING A ROTARY PART MOUNTED IN A ROLLER BEARING

(75) Inventor: Bernhard Kuhn, Biberach (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 403 days.

(21) Appl. No.: 10/426,355

(22) Filed: Apr. 28, 2003

(65) Prior Publication Data
US 2003/0190583 A1    Oct. 9, 2003

Related U.S. Application Data

(63) Continuation of application No. PCT/EP02/08933, filed on Aug. 9, 2002.

(30) Foreign Application Priority Data
Aug. 28, 2001 (EP) .................. 01120523
Feb. 28, 2002 (DE) .................. 102 08 692

(51) Int. Cl.
*A61C 1/05* (2006.01)
(52) U.S. Cl. ................. 433/132; 415/904
(58) Field of Classification Search ............... 433/126, 433/131, 132, 114; 415/904
See application file for complete search history.

(56) References Cited

U.S. PATENT DOCUMENTS 4,231,739 A * 11/1980 Iudica ........................ 433/126
4,249,896 A * 2/1981 Kerfoot, Jr. ................. 433/132
4,941,828 A * 7/1990 Kimura ....................... 433/114
5,507,642 A * 4/1996 Wohlgemuth ............... 433/132
5,676,542 A * 10/1997 Lingenhole et al. ........ 433/115
5,779,474 A * 7/1998 Gonser ........................ 433/129
6,120,291 A * 9/2000 Bareth et al. ................ 433/132

FOREIGN PATENT DOCUMENTS

CH           690226 A5      6/2000
FR           1316974        2/1963
WO           WO 01/01879 A1 1/2001

OTHER PUBLICATIONS

International Search Report in PCT/EP02/08933 dated Nov. 5, 2002.

* cited by examiner

*Primary Examiner*—Todd E. Manahan
(74) *Attorney, Agent, or Firm*—Marshall, Gerstein & Borun LLP

(57) ABSTRACT

The invention relates to a medical or dental-medical handpiece having a rotary part which is rotatably mounted in a bearing bush by means of a roller bearing having an inner ring and an outer ring. In order to improve the handpiece with regard to an axial limiting of the roller bearing there is arranged in the inner surface of the bearing bush or in the outer surface of the outer ring a first ring groove in which there sits a securing ring which projects out of the first ring groove and bears at least with its one side on a shoulder surface of the respective radially oppositely lying part.

27 Claims, 4 Drawing Sheets

Figure 1:
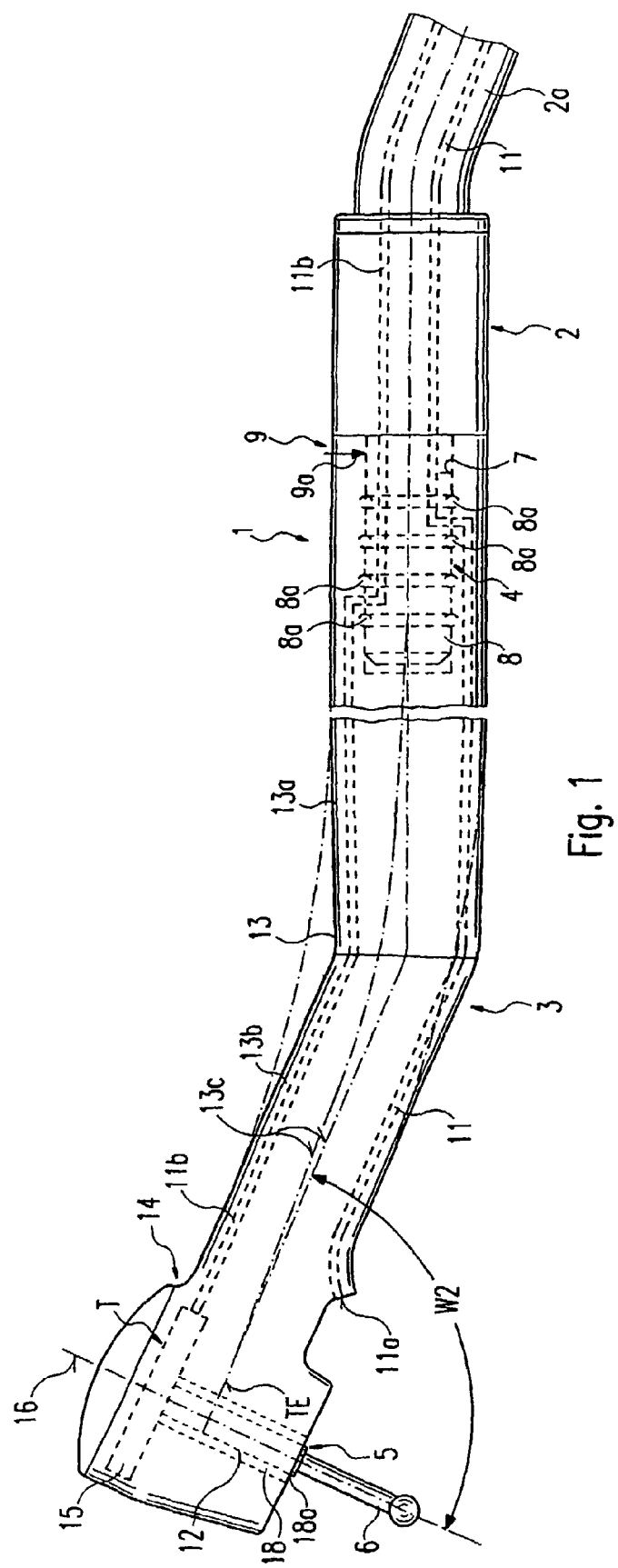

MEDICAL OR DENTAL-MEDICAL HANDPIECE HAVING A ROTARY PART MOUNTED IN A ROLLER BEARING

This is a continuation of International Application No. PCT/EP02/08933 filed Aug. 9, 2002, the entire disclosure of which is incorporated herein by reference.

The invention relates to a medical or dental-medical handpiece.

A medical or dental-medical handpiece is an object which is put to use for working the human body or natural or artificial parts thereof, such as prostheses, with a tool. The tool is in most configurations a material removing tool which acts on the body with a rotational movement or with a movement going back and forth. As drive there serves a rotational motor which may be arranged in the handpiece itself or in a so-called connection part with which the handpiece is releasably connected by means of a plug-in, in particular a plug-in/turn coupling having a coupling recess in one the one part and a coupling pin, engaging the coupling recess, on the other part. Also in the presence of a back and forth going tool drive, the drive movement is derived from a rotary movement which at least one rotary part carries out and for this purpose is rotatably mounted in the inner ring of a roller bearing having the inner ring and an outer ring. For axially positioning the inner ring and/or the outer ring of the roller bearing it is usual to provide shoulder surfaces on which the roller bearing ring concerned bears and thus is restricted against an axial movement.

It is further known to provide, for the axial sealing of the gap between an outer ring and a bearing bushing surrounding it, a sealing ring of elastic material which sits in an inner ring groove in the inner surface of the bearing bushing and presses elastically against the outer surface of the outer ring. Such a configuration can be taken for example from WO 01/01879 A1. Here, there is also involved the type of construction of a handpiece indicated in the introduction. The arrangement of shoulder surfaces for the axial restriction of an outer ring and/or inner ring of the roller bearing makes the construction of a handpiece of the kind concerned more difficult, since because of the at least one shoulder surface in each case a particular installation and removal direction is predetermined for the roller bearing.

The object of the invention is to improve a medical or dental-medical handpiece of the kind indicated in the introduction with regard to the axial restriction of its roller bearing, or its outer and/or inner ring. Further, the object of the invention is to improve a roller bearing with regard to the same purpose.

Due to the form-fitting co-operation of the securing ring with the shoulder surface the ring opposes an axial movement of the roller bearing concerned with a resistance which ensures the axial securing or positioning of the roller bearing ring concerned. Since both rings of the roller bearing stand in form-fitting engagement against an axial displacement, through the roller bodies, the axial securing or positioning applies beyond the roller bearing ring concerned also for the overall roller bearing.

There is particularly suitable as securing ring one of such a circular cross-section for which the term O-ring has established itself in the language of this technical field. With such a securing ring the side towards the roller bearing ring concerned is convexly rounded. This is favourable upon mounting of the roller bearing ring concerned because the securing ring forms of itself, with its rounded flanks, lead-in surfaces which ensure that upon the mounting of the roller bearing ring concerned these lead-in surfaces ensure a self-acting pressing away of the ring section of the securing ring standing in the path, whereby in the mounted end position the securing ring self-actingly goes into the second ring groove due to its elasticity. There may be provided further lead-in surfaces at the ends of the roller bearing ring concerned or also at the edges of the bearing bushing. With such a configuration a self-acting pressing away of the overstanding ring section is possible even in the case of a considerable radial projection of the securing ring in the relaxed condition.

Various requirements are placed upon an axial securing or positioning of the roller bearing. In many applications the arrangement can be such that an axial securing is present solely to the effect that the roller bearing ring concerned is held axially so that it cannot be lost. The elastic supporting of the securing ring in accordance with the invention at the shoulder surface concerned however makes possible also a defined axial positioning of the roller bearing ring concerned, whereby although due to the elastically compressible material of the securing ring, no great axial forces can be taken up, this is however not even necessary in many mounting situations. If an axial positioning of the roller bearing ring concerned is desired, it is advantageous to provide for this a one-sided support shoulder and to offset the annular groove in the roller bearing ring with reference to the securing ring towards the axial direction away from the shoulder surface so far that the securing ring engages eccentrically in the ring groove of the roller bearing ring and through this exercises an elastic axial force on the roller bearing ring, which acts on the roller bearing ring against the shoulder surface or holds it in abutment with the shoulder surface.

The form-fitting engagement of the securing ring in accordance with the invention into the second ring groove also makes possible a radially elastic mounting. For this case there is to be provided between the roller bearing ring and the bearing bushing or the bearing pin a radial spacing in the region of which a radial movement is ensured due to the elasticity of the securing ring. Further features of various embodiments make possible a simple, small and economically producible manner of construction, which is suitable in particular for the restricted space situation in a handpiece of the kind concerned. Further, there is made possible a simple assembly and disassembly.

Below, advantageous configurations of the invention will be described in more detail with reference to exemplary embodiments and drawings.

Figure 2:
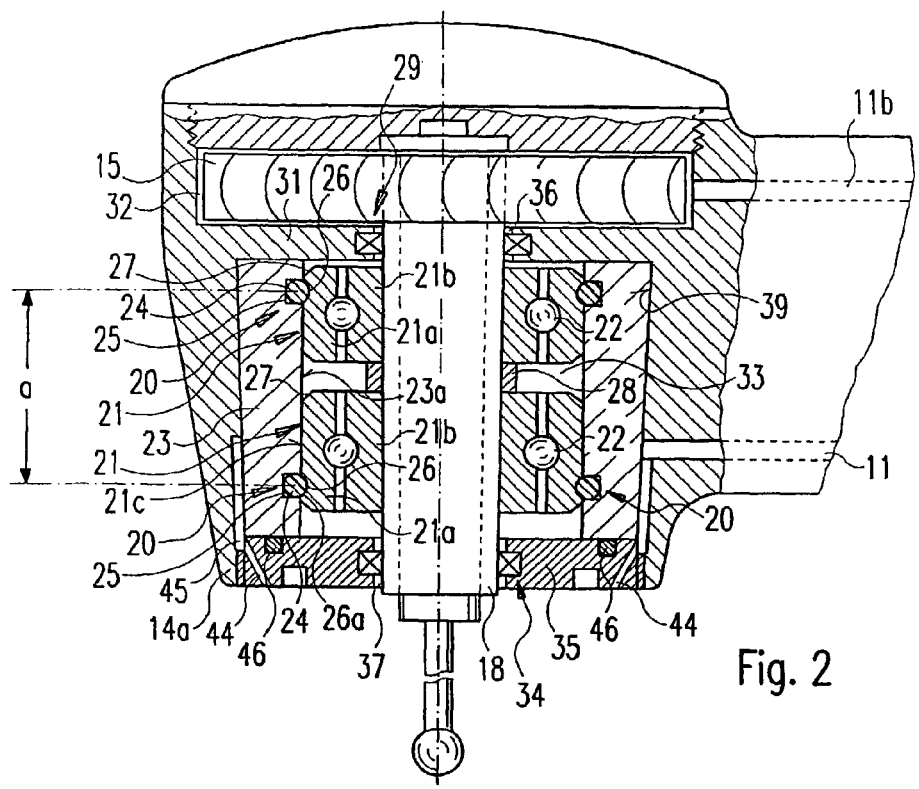
Figure 3:
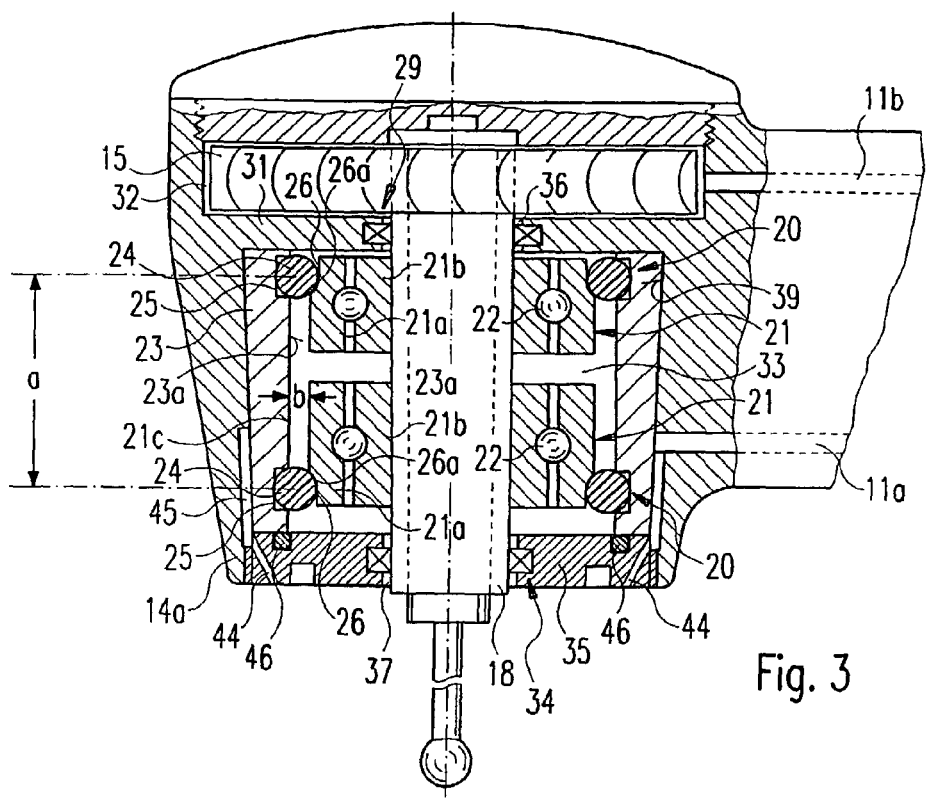
Figure 4:
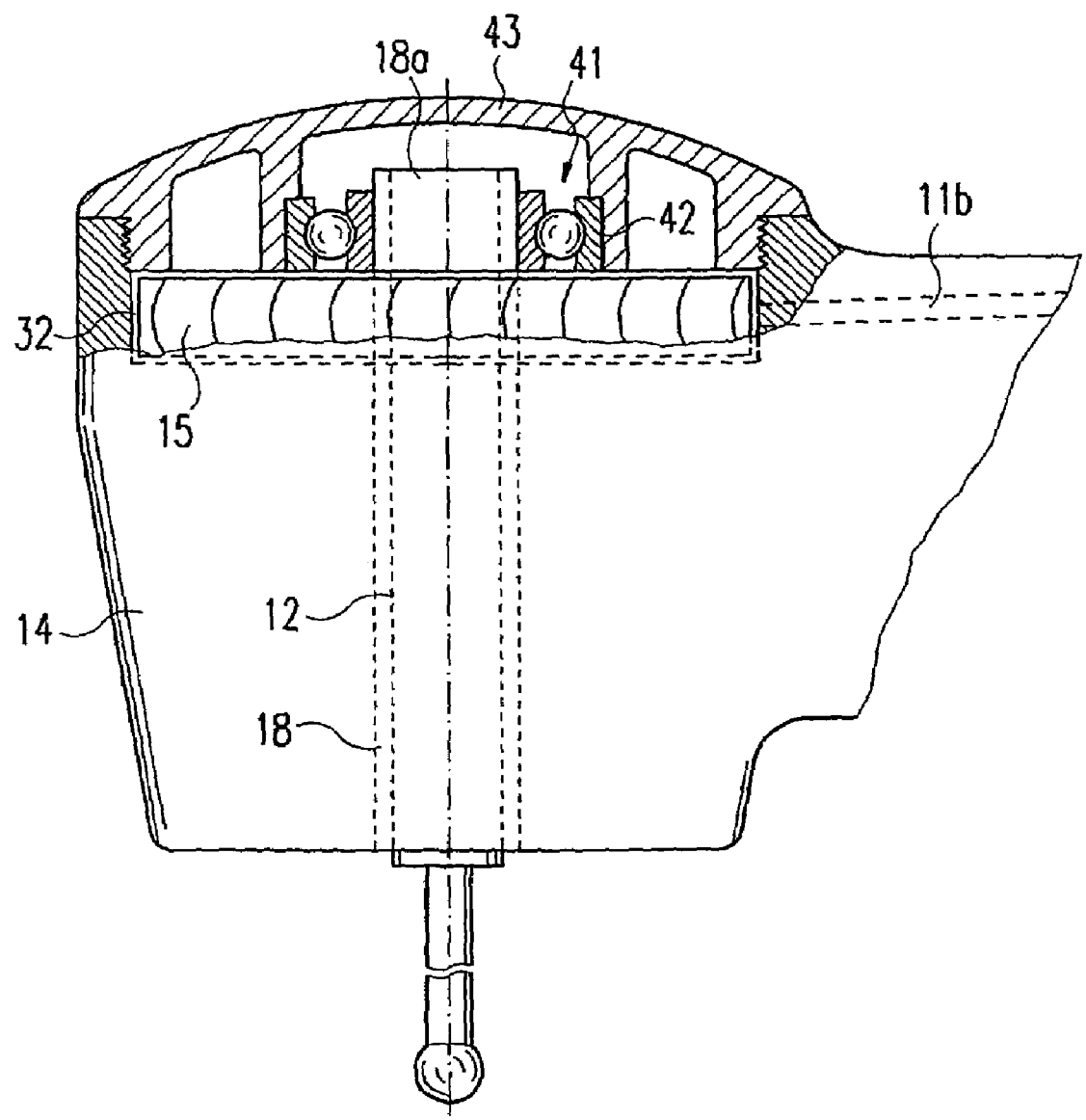
Figure 6:
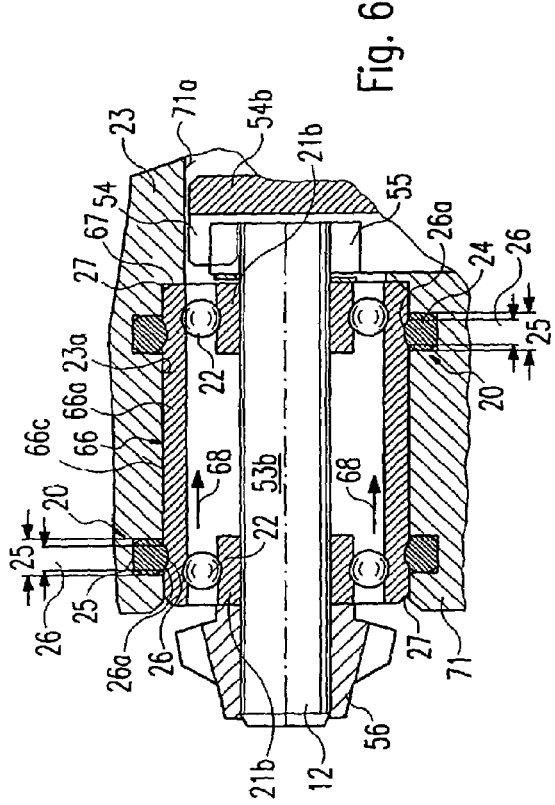
Figure 5:
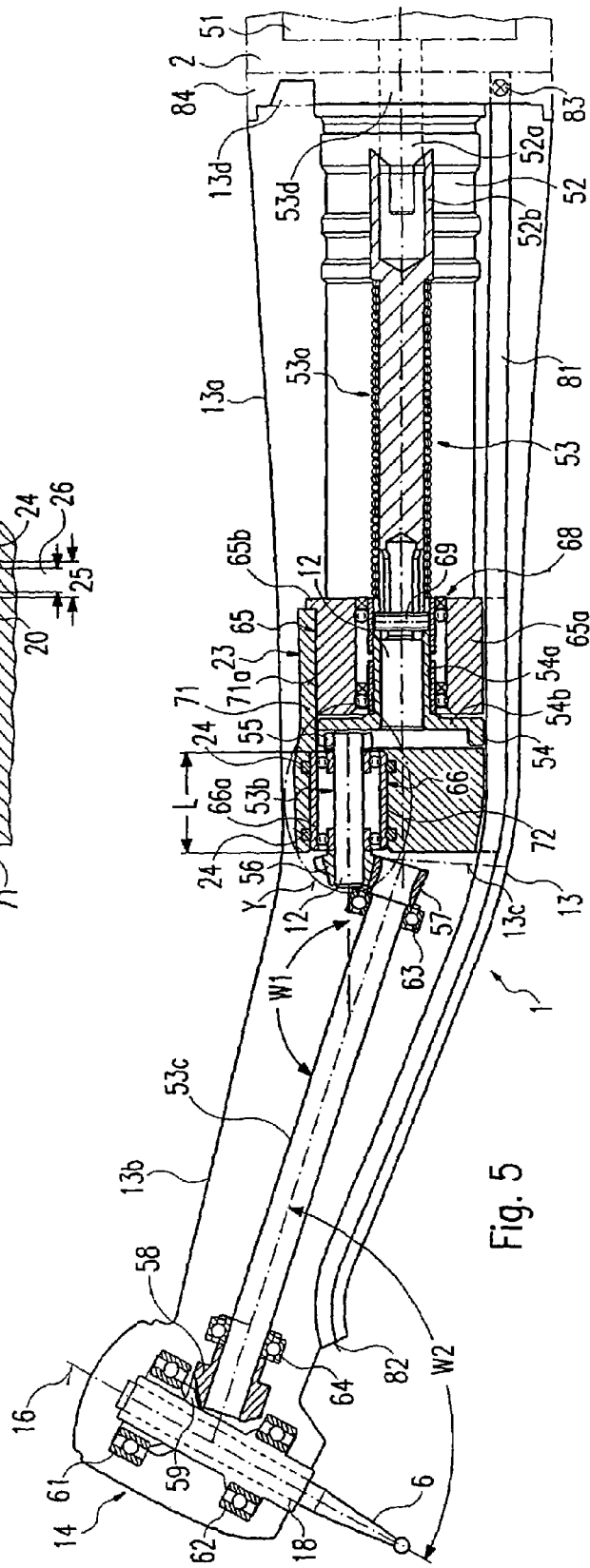

There is shown:

FIG. 1 a handpiece in accordance with the invention, in a side view, which together with a so-called connection part forms a treatment instrument;

FIG. 2 the head of the handpiece in axial section;

FIG. 3 the head of the handpiece in a modified configuration, in axial section;

FIG. 4 the head of the handpiece in a further modified configuration, in axial section;

FIG. 5 a handpiece a in further modified configuration, in axial section;

FIG. 6 the middle region, designated by Y, of the handpiece according to FIG. 5, in axial section to an enlarged scale.

The treatment instrument, designated in its entirety by 1 in FIG. 1, consists of a rearward instrument part, namely a so-called connection part 2, and a forward instrument part, namely the so-called handpiece 3, which are releasably connected with one another by means of a coupling 4 in particular a plug-in coupling, preferably a plug-in/turn coupling. With the present exemplary embodiment there is arranged at the forward end of the treatment instrument 1 a holder device 5 for a tool 6, whereby the tool 6 may stand out to the side or forwardly. The handpiece may extend straight (not illustrated) or curved (indicated by chain lines) to the side away from the tool 6, or angle shaped. The plug-in/turn coupling is formed by means of a coupling recess 7, round in cross-section, and in coupling pin 8 which can be inserted therein with slight play for movement. With the present exemplary embodiment, the coupling recess 7 is arranged at the rearward end of the handpiece 3, and the substantially cylindrical coupling pin 8 extends from the connection part 2 forwardly. In the coupled condition the coupling recess 7 and the coupling pin 8 are releasably latched to one another by means of a latching device 9. This has a latching element 9 which is mounted radially moveably in the one coupling part and is biassed by means of a spring force into a latching position, crossing the dividing gap, in which the latching element 9a engages into a ring groove in the other coupling part. Such a latching device 9 is self-actingly latched upon coupling and upon uncoupling can be overcome by the manual exercise of an axial pulling force, whereby the latching element 9a is self-actingly forced into its release position.

The connection part 2 is connected with a flexible supply line 2a, which is connected with a non-illustrated control apparatus. The handpiece 3 is preferably freely rotatably mounted on the coupling pin 8, through which handling is improved. Through the plug-in/turn coupling 4 there extends at least one media line 11 for a treatment or drive medium, e.g. water, compressed air, or a water/air mixture (spray). The media line 11 can extend axially through the radial dividing gap (not illustrated) or Z-shaped through a hollow cylindrical dividing gap between the coupling recess 7 and the coupling pin 8, whereby the media line 11 crosses the dividing gap in the region of a ring groove in the coupling pin 8 or in the coupling recess 7, so that in any rotary position the passage of media is ensured. To both sides of the passage, the dividing gap is sealed by means of a sealing ring 8a which may be arranged in a ring groove in the wall of the coupling recess 7 or in the outer surface of the coupling pin 8. Through this a free rotatability through 360E and more is ensured. The media line 11 extends from the rearward end of the treatment instrument 1 to its forward end region, whereby it may run partially as a channel in the instrument body or as a tube or pipeline. The media line 11 opens out in the forward end region of the treatment instrument 1, out of this, whereby the outlet opening 11a is directed towards the treatment site or to the tip of the tool 6.

With all exemplary embodiments of the invention, for which the same or similar parts are provided with the same reference signs, the handpiece 3 has a rotary part 12 mounted rotatably therein in a roller bearing. With the exemplary embodiment according to FIG. 1 there is involved a so-called turbine handpiece with an arc-shaped curved or angled shaft 13. This can be formed in one piece or consist of a rearward and a forward shaft section 13a, 13b, which are fixedly connected with one another at the beginning of the arc or at the apex of the angle. At the forward end of the shaft 13 there is located a thickened head 14 in which a turbine T is arranged with a turbine wheel 15 which is rotatably mounted in the head 14 around an axis of rotation 16 extending transversely of the shaft 13 or its longitudinal middle axis 13c and in the angle or base plane of the shaft 13. The turbine wheel 15 is located in a turbine chamber 17 into which a media line 11b for compressed air opens and is directed towards the blades of the turbine wheel 15. The media line 11b passes through the plug-in/turn coupling 4 likewise in a Z-shape. The turbine wheel 15 is connected with the holder device 5, here with a receiving sleeve 18, in which the tool 6 can be inserted with its shaft and can be releasably fixed in a manner known per se by means of a fixing device.

The turbine wheel 15 and the receiving sleeve 18 may be formed in one piece. With the exemplary embodiment according to FIG. 1 the turbine wheel 15 is connected with the receiving sleeve 18 in the end region thereof away from the plug-in opening 18a. For rotary mounting of the turbine rotor 15a consisting of the turbine wheel 15 and the receiving sleeve 18 there is or are provided one or two roller bearings 21 (FIG. 2) arranged next to one another having an outer ring 21a and an inner ring 21b and roller bodies, in particular balls, arranged therebetween, with which the turbine rotor 15a is mounted rotatably about the axis of rotation 16 in a bearing bushing 23 arranged in the housing of the head 14. For axially securing or positioning, there is associated with each roller bearing 21 in the bearing bushing 23 a securing device 20 having a securing ring 24 of elastically deformable or elastically compressible material, which is arranged so deep in a ring groove 25 in the inner surface 23a of the bearing bushing 23 that it projects beyond the inner surface 23a and thus forms a securing bead with which it sits in a ring groove 26, lying radially opposite the ring groove 25, in the outer surface 21c of the roller bearing outer ring 21a. Preferably the securing ring 24 presses radially inwardly against the bottom of the ring groove 26 with a for example small elastic bias force. This can be achieved in that the inner diameter of the securing ring 24 is smaller than the inner diameter of the ring groove 26 and/or in that the half difference between the inner diameter of the ring groove 26 and the outer diameter of the ring groove 25 is somewhat smaller than the diameter of the securing ring 24, which is preferably round in cross-section. In both cases, the securing ring 24 is elastically biased radially inwardly against the bottom of the ring groove 26. For improving the axial positioning it is also advantageous if the axial width of the ring grooves 25, 26 is somewhat smaller than the axial dimension of the securing ring 24, so that this is elastically compressed between the side walls or flanks 26a of the ring groove 25, 26. With the exemplary embodiment, the cross-sectional form of the ring groove 25 is quadrilateral and the cross-sectional form of the ring groove 26 is rounded in the shape of a section of an arc of a circle. Other cross-sectional forms are however also possible.

For facilitating assembly, the roller bearings 21 have at least at one end side a rounded or acute angled lead-in surface 27, which upon axial insertion of the roller bearing 21 into the bearing bushing 23 self-actingly elastically deforms the securing ring 24 and self-actingly springs this again into the ring groove 26 in the mounted position. Preferably a lead-in surface 27 is provided at both end sides.

It is further advantageous to arrange the ring groove 26 axially offset with regard to the raceways of the roller bodies 22, through which the weakening of the material of the roller bearing outer ring 21a is of little or no effect. Preferably, the roller bearings 21 are similarly formed so that one roller bearing 21 can be selectively fit in the one or in the other bearing position, e.g. in a position rotated by 180E.

With the exemplary embodiment there are thus arranged two ring grooves 25, in each case with a securing ring 24, in the bearing bushing 23, the axial middle spacing a of which from one another is greater than the axial width of a roller bearing 21, whereby the ring grooves 26 are arranged in the end regions of the roller bearings 21 which are away from one another. They may, however, also be arranged, with regard to the roller bearings 21, in the middle or inwardly offset or in the two roller bearings 21 offset in an axial direction. With the exemplary embodiment there is present between the roller bearings 21 an axial spacing, which can be secured by means of a distancing ring 28.

If an axial securing of the roller bearing 21 is desired in only one axial direction, the ring groove 26 may be formed to axially run out to one side, as the exemplary embodiment according to FIG. 3, still to be described, shows per se. With that configuration, the flanks 26a of the ring groove 26 facing one another are adapted to the axial spacing of the securing rings 24 present and this preferably such that the securing rings 24 press with an elastic tension or compression against the preferably convergent flanks 26a.

The exemplary embodiment according to FIG. 3, with which the same or similar parts are provided with the same reference signs, differs from the exemplary embodiment according to FIG. 2 in that the roller bearing outer rings 21a are not received approximately flush with a usual roller bearing fit in the running bushing 23, but have a radial circumferential spacing b from the inner surface 23a. Through this, due to the elasticity of the securing rings 24, the mounting is elastically yielding not only in axial direction but also in radial direction, so that the turbine rotor 15a can elastically yield either axially or axially and radially, and thus is mounted axially elastically damped or also radial elastically damped. A further advantage is also here the simplified manner of construction and assembly or disassembly, with which the securing rings 24 after a displacement and deformation from, their securing position again self-actingly reshape and snap into their securing position, without having to be released and again put in place, as is the case with conventional securing rings of metal.

As FIGS. 2 and 3 allow further to be recognized, the roller bearings 21 are arranged in each case at an axial spacing from associated components of the head housing, so that the above-described axial yieldability is not restricted. If the axial yieldability is desired in only one axis direction, the roller bearing ring concerned may be restricted in the other axis direction by means of a bearing surface.

With the present exemplary embodiment, in which a turbine drive is provided, there is provided an axially effective ring seal 29 between the receiving sleeve 18 and a dividing wall 31 between the turbine chamber 32 and the inner chamber 33 of the running bushing 23. This may be a per se known sealing ring, which is received in a ring groove of the separating wall 31. A corresponding ring seal 34 may also be arranged between the receiving sleeve 18 and an end wall 35 of the head housing, which in the case of the exemplary embodiment is placed or screwed into the peripheral wall 14a of the head housing. The receiving sleeve 18 penetrates the separating wall 31 and the end wall 35 in holes 36, 37 with a corresponding play for movement.

In the case of both above-described exemplary embodiments, two roller bearings 21 are arranged axially next to one another. It is, however, also possible to form both roller bearings 21 by means of a single roller bearing or a single two-row roller bearing (not shown). It is further also possible to form the two roller bearing outer rings 21a by means of a common roller bearing outer ring of a two-row roller bearing, whereby the roller bearing inner rings 21b may remain unaltered as two rings arranged next to one another. When only one roller bearing or a two-row roller bearing or only one roller bearing outer ring is present, there is needed with the exemplary embodiment according to FIG. 2 only one securing ring 24 in order to attain an axial securing or positioning. This applies in principle also for the configuration according to FIG. 3 with the radial circumferential spacing d, but it is in this case advantageous, when only one roller bearing or only one roller bearing outer ring of a two-row roller bearing is present, to provide two securing rings 24 having an axial spacing from one another.

It is further possible to mount the roller bearing or bearings 21 directly on the circumferential wall 14a of the head housing, which in such a case forms the bearing bushing 23. With the above-described exemplary embodiments, the bearing bushing 23 is of hollow cylindrical shape and placed to fit in a receiving hole 39 bounded by the circumferential wall 14a and axially positioned, here by means of the end wall 35.

The exemplary embodiment according to FIG. 3, the diameter of the securing ring or rings 24 is greater, for example approximately by the amount b, than with the exemplary embodiment according to FIG. 2. Instead of the above-described one side mounting of the turbine rotor 15a, with regard to the turbine wheel 15, a two-sided mounting in accordance with FIG. 4 can also be provided, whereby the roller bearing 41 that is arranged on the side of the turbine wheel 15 away from the tool 6 may be a conventional radial bearing and/or an axial bearing. With the illustrated exemplary embodiment according to FIG. 4 there is provided a radial bearing which can also take up small axial loads and sits with its inner ring on a bearing pin 18a arranged on this side of the turbine wheel 15 and the outer ring of which is mounted in a mounting bore 42 of a lid 43 which can preferably be screwed into the head housing. With removed lid 43, the turbine rotor 15a can be removed out of the head housing upwardly. The rotary bearing on the side toward the tool 6 can be formed in accordance with FIG. 2 or 3 or in yet other manner.

The delivery of the at least one treatment medium, for example air or water or spray, can be effected through one or more outlet openings 44 arranged distributed around the circumference, which, openings are arranged in the circumferential wall 14a or in the end wall 35. With the exemplary embodiment, there is present a ring channel 45 in the circumferential wall 14a, surrounding the bearing bushing 23 in its end region toward the tool, which extends up to the end wall 35, whereby a plurality of media channels 46, distributed around the circumference and preferably running convergently, start from the ring channel 44 and pass through the end wall 35. The media line 11 opens out in the ring channel 44.

In order to prevent the penetration of the medium into the bearing chamber 33 of the bearing bushing 23 the joint arranged between the circumferential wall 14a and the bearing bushing 23 and/or the joint arranged between the end wall 35 and the bearing bushing 23 may be sealed in each case by means of a ring seal, for example by means of a O-ring 46, which sits in a ring groove which is arranged in one of the two parts in a manner known per se.

Instead of the arrangement of at least securing ring 24 between the roller bearing outer ring or rings 21a and the inner surface 23a of the bearing bushing 23 it is possible with both exemplary embodiments according to FIGS. 2 and 3 to arrange the securing ring or rings 24 in a corresponding arrangement between the roller bearing inner ring or rings 21b and the receiving sleeve 18, whereby there is arranged at least one groove, corresponding to the ring groove 25, in the outer surface of the receiving sleeve 18 and at least one ring groove 26 is arranged in the inner surface of the roller bearing inner ring 21b.

With the exemplary embodiment according to FIGS. 5 and 6, in which the same or similar parts are provided with the same reference signs, the elastically yielding—axially and if applicable also radially—mounting is arranged in the shaft 13 for the rotary mounting of a rotary part 12 rotatably mounted therein, here for the rotary mounting of a drive shaft longitudinal section. In the case of this treatment instrument 1, a drive motor 51, for example an electric motor, is arranged in the extended connection part 2, indicated by chain lines, and drivingly connected with the receiving sleeve 18 by means of a drive shaft or drive shaft train 53 having a plurality of drive shaft sections. In the region of the plug-in coupling 4 the drive shaft train 53 has a plug-in coupling 52 with two plug-in coupling elements 52a, 52b corresponding with one another in a form-fitting manner, whereby upon coupling and decoupling of the plug-in coupling 4 at the same time a coupling and decoupling of the plug-in coupling 52 is possible.

A drive shaft section 53a arranged in the rearward end region of the handpiece 3 extends up to the apex region of the angled shaft 13, whereby its forward end is connected with a third drive shaft section 53c by means of a second drive shaft section 53b extending axially in substance only in the apex region, which third drive shaft section extends in the forward shaft section 13b up to the receiving sleeve 18 and is drivingly connected therewith. For connecting the drive shaft sections 53a, 53b, 53c there is provided in each case a gear transmission. At the forward end of the first drive shaft section 53a there is arranged a gear 54 having an internal toothing, which meshes with a pinion 55 at the rearward end of the second drive shaft section 53b. Thereby, the second drive shaft section 53b is arranged, with regard to the apex 13c of the angling or curvature, offset towards the side away from the tool 6, whereby on the forward end of the second drive shaft section 53b and on the rearward end of the third drive shaft section 53c there is arranged in each case a pinion 56, 57 in substance in a transverse plane or overlapping one another, in the sense of spur or conical gears which mesh with one another. The second and the third drive shaft section 53b, 53c include an obtuse angle W1, which is open towards the side away from the tool 6.

The drive connection between the third drive shaft section 53c and the receiving sleeve 18 is formed by means of an angled gear transmission having a conical gear 58 at the forward end of the third drive shaft section 53c and conical gear 59 on the receiving sleeve 18. The tooth engagement between the conical gears 58, 59 is, with reference to the third drive shaft section 53c, arranged on its side away from the tool 6. Through this, the drive sleeve 18 is driven in the same direction of rotation as the first drive shaft section 53a. The receiving sleeve 18 is rotatably mounted by means two roller bearings 61, 62 in the head 14, which have a spacing from one another directed longitudinally of the axis of rotation 16, which spacing is larger than the conical gear 58, so that the latter can be arranged therebetween, including the conical gear 59, which is arranged on the side of the conical gear 58 away from the tool 6 and at the same time on the side of the roller bearing 61 towards the tool 6, and which is arranged further distant from the tool 6 than the other roller bearing 62. For rotary mounting of the second drive shaft section 53c there is arranged in each case a roller bearing 63, 64 on the end regions of this drive shaft section 53c, the outer rings of which are seated and mounted in a non-illustrated longitudinal hole of the shaft section 13b.

The configuration of the gear 54 as a hollow gear makes possible with radially small manner of construction, a relatively great gearing up of the speed of rotation between the first and the second drive shaft section 53a, 53b.

With the exemplary embodiment according to FIGS. 5 and 6 there are provided for mounting the first drive shaft section 53a and the second drive shaft section 53b in each case in the shaft, a two-row roller bearing 65, 66 in a bearing bushing. This roller bearing 65, 66 is sufficient in each case to mount the entire drive shaft section 53a or 53b sufficiently stably. The first drive shaft section 53a projects beyond the roller bearing 65 freely outstanding rearwardly, whereby a slight radial flexibility is present for coupling with the drive shaft section of the connection part 2. For increasing the flexibility there may be connected between the first drive shaft section 53a and gear 54 a joint connection 68 having a transverse pin 69, whereby the radial flexibility of the first drive shaft section 53a is increased. The gear 54 consists of a rearward cylindrical or hollow cylindrical mounting section 54a at the forward end of which a flange 54b is arranged which carries at its forward side a hollow gear crown 54.

The roller bearings 65, 66 may have two roller bearing inner rings 21b, for example having an axial spacing from one another, or also one axially through-going roller bearing inner sleeve (not illustrated).

With all roller bearings 65, 66 the axial spacing of the roller rows from one another can be advantageously greater than the mean diameter of the roller body raceways. The roller bearing 66 is so long, see L, that it fits between the pinions 55, 56, whereby at the same time an axial restriction is constituted for the second drive shaft section 52b.

Both roller bearings 65, 66 are preferably mounted in a common carrier body 71 forming a bearing bushing 23, which sits in the shaft 13 in the region of the rearward shaft section 13a neighbouring the apex point, is mountable from the rear and again dismountable from the rear, or vice versa, through a rearwardly or forwardly opening receiving hole 71a, and is axially fixable in the shaft section 13a in a manner not illustrated.

As can be further understood from FIGS. 5 and 6, the rearward roller bearing 65 is in inserted from the rear into the receiving hole 71a of the carrier body 71 and for example by means of a flange 65b arranged at the rearward end of the outer bearing sleeve 65a axially fixed towards the fore. The forward roller bearing 66 is, in contrast, placed from the fore into a receiving hole 72 of the carrier body 71 and axially fixed or positioned in the above-described sense by means of one or two securing rings 24. The flange forming the gear 54 is mounted in the receiving hole 71a between the roller bearing 65 and the bottom of the receiving hole 71 with play for movement.

With the exemplary embodiment according to FIGS. 5 and 6 there is associated with the outer bearing sleeve 66a in its outer surface 66c of the for example single and two-row roller bearing 66, at least one, preferably two, securing rings 24 having an axial spacing from one another, whereby this can be formed in the configuration according to FIG. 2 or 3. In FIGS. 5 and 6 only the configuration according to FIG. 2 is illustrated. In order to avoid repetition in this respect reference is made to the description of the exemplary embodiments according to FIGS. 2 and 3.

With the configuration according to FIG. 6, however, the following special feature is provided. On the one hand, the roller bearing outer ring, here the common outer mounting sleeve 66a, is positioned at one of its ends, here at its rearward end, at a shoulder 67 in the carrier body 71, which shoulder may be formed by means of a step surface in the bore receiving the outer bearing sleeve 66a. Further, the at least one ring groove 26 is, upon abutment of the outer bearing sleeve 66a on the shoulder 67, offset towards the axial direction away from the shoulder 67, with regard to the associated ring groove 25, which can be clearly seen from FIG. 6. Through this offset, the securing ring 24 is non-symmetrically deformed with regard to its ring plane, whereby due to its elasticity its seeks to take its symmetrical form. Through this the securing ring 24 generates an axial force, see arrow 68, which elastically biasses the outer bearing sleeve 66a against the shoulder 67 and thus ensures its bearing on the shoulder 67.

A further advantage of the securing or positioning device 20 consists in that through the securing ring 24 a ring seal for the sealing off of the gap between the inner surface 23a and the bearing pin is formed, and in particular then when the securing ring 24 is elastically biassed not only against the bottom of the ring groove 26 but also against the bottom the ring groove 25.

81 designates a light conductor rod, which extends in the vicinity of the edge of the tool side of the shaft 13 in the shaft from the rear forwardly to the outlet window 82 directed towards the free end of the tool 6. In functional operation of this handpiece 3 light is coupled in from a light source 83 into the light conducting rod 81, whereby the light source 83 is arranged on a carousel 84 (schematically illustrated) rotatably mounted in or on connection part 2, which carousel is form-fittingly connected with the handpiece 3 by means of a carrier 13d, so that also in this case the free rotatability of the handpiece 3 in the plug-in/turn coupling 4 is ensured.

The angle W2 in FIG. 5 included between the middle axis of the forward shaft section 13b and the axis of rotation 16 of the receiving sleeve 18 is more than 90E, preferably substantially 100E. Such a configuration is, taking into account the anatomy in the mouth of the patient, particularly favourable. This favourable configuration with the angle W2 equal to approximately 100E applies not only for the handpiece 3 according to FIG. 5 operable with a motor in the connection part 2, but also for the turbine handpiece 3 in accordance with FIG. 1.

The configurations in accordance with the invention are also suited particularly well for a handpiece that is not formed with an angle shaped, such as is illustrated in FIG. 1, but is curved in its forward region in an arc shape, whereby the apex 13c may be arranged in the curve middle or at the end of the curve away from the tool 6.

The angle W2 more than 90E and preferably substantially 100E, in the case of the curved shape of the handpiece 3, extends between the middle axis of the holder device 5 and a tangential plane TE in which the curve middle axis 13c of the handpiece 3, indicated by chain lines in FIG. 1, cuts the middle axis 16 of the holder device 5.

The outer ring 65a can, by means of securing device corresponding to the securing device 20 in accordance with FIG. 6 but rotated by 180E, be secured against an unintended displacement directed rearwardly, which is not shown in FIG. 5.

The securing device 20 in accordance with the invention can also be arranged between the inner ring 21b and the rotary part 12 in configurations corresponding to the above-described configurations.

The invention claimed is:
1. Medical or dental-medical handpiece comprising:
   a shaft;
   a drive shaft section rotatably mounted in the shaft in a bearing bushing by means of a roller bearing having an inner ring and an outer ring, the outer ring having an outer surface, the bearing bushing having an inner surface;
   a first ring groove disposed in the bearing bushing inner surface or in the outer surface of the roller bearing outer ring;
   a securing ring sitting in and projecting outwardly from the first ring groove and bearing at least with one side thereof on a shoulder surface of a radially opposed part, and
   a second ring groove axially offset in the axial direction away from a bounding surface;
   wherein the roller bearing outer ring bears axially on the bounding surface.

2. Handpiece of claim 1, wherein the securing ring is elastically biased against said shoulder surface.

3. Handpiece of claim 1, wherein the shoulder surface is formed by a second ring groove having two shoulder surfaces and a bottom surface in the radially opposed part and the securing ring bears on both shoulder surfaces of the second ring groove.

4. Handpiece of claim 3, wherein the securing ring is elastically biased against one said shoulder surface and also against the bottom surface of the second ring groove.

5. Handpiece of claim 4, wherein the securing ring bears on the bottom surface of the second ring groove and a ring gap is defined between the inner surface of the bearing bushing and the outer surface of the outer ring.

6. Handpiece of claim 5, wherein the securing ring is elastically biased against the bottom surface of the second ring groove.

7. Handpiece of claim 3, wherein the part having the second ring groove or the outer ring has at least one axial edge with a rounded or oblique lead-in surface.

8. Handpiece of claim 1, wherein the first ring groove or the at least one shoulder surface is axially offset with respect to a raceway defined in the outer ring.

9. Handpiece of claim 1, wherein the second ring has a cross-sectional shape that is rounded or has convergent flanks.

10. Medical or dental-medical handpiece comprising:
   a rotary part forming a tool-receiving sleeve or a turbine rotor, the sleeve or rotor being rotatably mounted in a bearing bushing by means of a roller bearing having an inner ring and an outer ring, the bearing bushing having an inner surface and the roller bearing outer ring having an outer surface with two roller bearings disposed in the bearing bushing axially adjacent each other or a two-row roller bearing disposed in the bearing bushing; and
   a first ring groove disposed in the bearing bushing inner surface or in the outer surface of the respective roller bearing outer ring, with a securing ring sitting in and projecting outwardly from the first ring groove and bearing at least with one side thereof on a shoulder surface of a radially opposed part;
   wherein the shoulder surface is formed by a second ring groove having two shoulder surfaces and a bottom surface in the radially opposed part and the securing ring bears on both shoulder surfaces of the second ring groove; and
   wherein the outer ring bears axially on a bounding surface and the second ring groove is axially offset in the axial direction away from the bounding surface.

11. Handpiece of claim 10, wherein the securing ring is elastically biased against one said shoulder surface.

12. Handpiece of claim 10, wherein the securing ring is elastically biased against one said shoulder surface and also against the bottom surface of the second ring groove.

13. Handpiece of claim 12, wherein the securing ring bears on the bottom surface of the second ring groove and a ring gap is defined between the inner surface of the bearing bushing and the outer surface of the outer ring.

14. Handpiece of claim 13, wherein the securing ring is elastically biased against the bottom surface of the second ring groove.

15. Handpiece of claim 10, wherein the part having the second ring groove or the outer ring has at least one axial edge with a rounded or oblique lead-in surface.

16. Handpiece of claim 10, wherein the first ring groove or the at least one shoulder surface is axially offset with respect to a raceway defined in the outer ring.

17. Handpiece of claim 10, wherein the second ring has a cross-sectional shape that is rounded or has convergent flanks.

18. Medical or dental-medical handpiece comprising:
a bearing bushing;
a rotary part rotatably mounted in the bearing bushing by means of a roller bearing having an inner ring and an outer ring, the bearing bushing having an inner surface and the outer ring having an outer surface;
a first ring groove disposed in the bearing bushing inner surface or in the outer surface of the roller bearing outer ring; and
a securing ring sitting in and projecting outwardly from the first ring groove and bearing at least with one side thereof on a shoulder surface of a radially opposed part,
wherein the roller bearing outer ring bears axially on a bounding surface and a second ring groove is axially offset in the axial direction away from the bounding surface.

19. Handpiece of claim 18, wherein the securing ring is elastically biased against said shoulder surface.

20. Handpiece of claim 18, wherein the shoulder surface is formed by a second ring groove having two shoulder surfaces and a bottom surface in the radially opposed part and the securing ring bears on both shoulder surfaces of the second ring groove.

21. Handpiece of claim 20, wherein the securing ring is elastically biased against one said shoulder surface and also against the bottom surface of the second ring groove.

22. Handpiece of claim 21, wherein the securing ring bears on the bottom surface of the second ring groove and a ring gap is defined between the inner surface of the bearing bushing and the outer surface of the outer ring.

23. Handpiece of claim 22, wherein the securing ring is elastically biased against the bottom surface of the second ring groove.

24. Handpiece of claim 20, wherein the part having the second ring groove or the outer ring has at least one axial edge with a rounded or oblique lead-in surface.

25. Handpiece of claim 20, wherein the outer ring bears axially on a bounding surface and the second ring groove is axially offset in the axial direction away from the bounding surface.

26. Handpiece of claim 18, wherein the first ring groove or the shoulder surface is axially offset with respect to a raceway defined in the outer ring.

27. Handpiece of claim 18, wherein the second ring has a cross-sectional shape that is rounded or has convergent flanks.

* * * * *